United States Patent [19]

Stelzer

[11] Patent Number: 4,486,374
[45] Date of Patent: Dec. 4, 1984

[54] PROCESS FOR SOFTENING AN ABSORBENT LAMINATE

[75] Inventor: Paul H. Stelzer, Granville, Ohio

[73] Assignee: The Dow Chemical Company, Midland, Mich.

[21] Appl. No.: 434,686

[22] Filed: Oct. 15, 1982

[51] Int. Cl.$^3$ .......................... B29D 7/20; B29C 25/00
[52] U.S. Cl. ..................................... 264/156; 264/343
[58] Field of Search ........... 264/154, 156, 232, 331.12, 264/331.18, 341, 343, 340, DIG. 62, DIG. 47, 138; 8/130.1; 128/156; 604/368; 428/300

[56] References Cited

U.S. PATENT DOCUMENTS

| | | | |
|---|---|---|---|
| 3,926,891 | 12/1975 | Gross | 260/29.6 E |
| 3,980,663 | 9/1976 | Gross | 260/29.6 TA |
| 4,066,078 | 1/1978 | Berg | 128/2.06 E |
| 4,076,673 | 2/1978 | Burkholder | 260/29.2 EP |
| 4,128,686 | 12/1978 | Kyle | 428/219 |
| 4,263,363 | 4/1981 | Buck | 428/284 |
| 4,269,188 | 5/1981 | Nishizawa | 128/287 |
| 4,310,593 | 1/1982 | Gross | 428/290 |
| 4,413,995 | 11/1983 | Korpman | 604/368 |

*Primary Examiner*—James Lowe

[57] ABSTRACT

Laminates of film of a hydrophilic polymer and adhered substrates are softened by applying a nonvolatile aliphatic compound to at least one surface.

17 Claims, No Drawings

PROCESS FOR SOFTENING AN ABSORBENT LAMINATE

BACKGROUND OF THE INVENTION

This invention relates to a process for improving the flexibility of absorbent laminates of water-swellable hydrophilic polymer film bonded to wicking substrates.

It is known from U.S. Pat. No. 3,669,822 dated June 13, 1972 that tissue/polyethylene film/tissue laminates can be crimped or embossed to give an improved hand or flexibility or tissue-like feel.

It is also known from French Pat. No. 2,375,985 dated Sept. 1, 1978 that nonwoven fiber sheet/tissue/absorbent layer/tissue/polyethylene film laminates can be made flexible with adhesion to the film by adding an adhesive between the tissue and the polyethylene film followed by transverse creasing or crimping.

In U.S. Pat. Nos. 4,117,184 and 4,176,667, it is disclosed that tissue/aerated absorbent film/tissue laminates can be prepared.

While the laminates disclosed in U.S. Pat. No. 4,117,184 have good absorption rates for water, urine and other body fluids or exudates, they have a tendency to become brittle and inflexible in atmospheres of low relative humidity. The result is an unacceptable rattle sound when the laminate is flexed and the laminate has a stiff or board-like feel.

SUMMARY OF THE INVENTION

Laminates comprising a central film of a lightly cross-linked, water-swellable hydrophilic polymer combined with wicking substrates are softened and made more flexible by applying an aliphatic hydroxy compound to at least one surface.

DETAILED DESCRIPTION OF THE INVENTION

While the absorbent film can be a solid film as in U.S. Pat. No. 4,076,673, dated Feb. 28, 1978, it is preferably an aerated film as disclosed in U.S. Pat. No. 4,117,184. The film will generally be between 0.1 to 10 mils in thickness, preferably from 1 to 3 mils.

The water-swellable, lightly cross-linked hydrophilic polymers useful in this invention can be any of the known hydrophilic polymers that are capable of being formed into a film. Examples of such polymers are disclosed in U.S. Pat. Nos. 3,997,484; 3,926,891; 3,935,099; 4,090,013 and 4,190,562.

The preferred hydrophilic polymers useful in this invention are polyelectrolytes and must be essentially water soluble in the salt form. Examples of useful polyelectrolytes include ammonium or alkali metal salts of homopolymers of acrylic or methacrylic acid and copolymers with one or more ethylenically unsaturated comonomers.

Preferably the polyelectrolyte is a partially saponified polyacrylate polymer. The polymer before saponification is the result of reacting together a mixture of monomers which comprises (1) 30 to 92 percent by weight of an alkyl acrylate wherein the alkyl group has from 1 to 10 carbon atoms, an alkyl methacrylate wherein the alkyl group has from 4 to 10 carbon atoms, or mixtures thereof; (2) 8 to 70 percent by weight of an olefinically unsaturated carboxylic acid and (3) 0 to 15 percent by weight of an omega hydroxyalkyl acrylate wherein the hydroxyalkyl group has from 1 to 4 carbon atoms.

Examples of useful alkyl acrylates include methyl acrylate, ethyl acrylate, propyl acrylate, butyl acrylate and hexyl acrylate. Examples of useful alkyl methacrylates include methyl methacrylate, ethyl methacrylate, hexy methacrylate, octyl methacrylate and decyl methacrylate. Examples of useful omega hydroxyalkyl acrylates include 2-hydroxyethyl acrylate, hydroxymethyl acrylate, 3-hydroxypropyl acrylate and 4-hydroxybutyl acrylate.

The olefinically unsaturated carboxylic acids useful in this invention are mono- or polycarboxylic acids. Examples of monocarboxylic acids include acrylic acid, methacrylic acid, crotonic acid and isocrotonic acid. Examples of polycarboxylic acids include maleic acid, fumaric acid and itaconic acid.

The foregoing polyacrylates are then dissolved in an aqueous alkali metal hydroxide solution. The amount of hydroxide solution employed is sufficient to saponify some of the acrylate esters to alkali metal carboxylates and to neutralize the carboxylic groups of the copolyacrylate to alkali metal carboxylates so that the saponified polyacrylate polymer has from 30 to 70 weight percent alkali metal carboxylates.

The partially saponified polyacrylate polymer is employed as a solution containing 5 to 60 percent by weight of the polymer.

A list of applicable polymers which could be prepared from readily available monomers and converted into their salt form is as follows:

| | |
|---|---|
| acrylic acid | acrylate copolymers |
| acrylic acid | acrylamide copolymers |
| acrylic acid | olefinic copolymers polyacrylic acid |
| acrylic acid | styrene sulfonic acid copolymers |
| acrylic acid | vinyl acetate copolymers |
| acrylic acid | vinyl alcohol copolymers | and copolymers of methacrylic acid with all the above comonomers.

Illustrative examples of the polyfunctional cross-linking agents useful in this to convert the above polyelectrolytes into a water-swellable polymers invention are set forth in U.S. Pat. Nos. 2,926,154; 3,224,986 and 3,332,901. These polyfunctional cross-linking agents are generally known as polyamide-polyamine epichlorohydrin adducts. The disclosures of these references are incorporated herein by reference. Similar cross-linking agents are available from Hercules Incorporated as Kymene 557 ® and Polycup 172 ®. The structure of these adducts has been discussed in an article by M. E. Corr et al., "Journal of Applied Polymer Science," Vol. 17, pages 721–735 (1973).

Illustrative examples of the difunctional agents useful in this invention are polyhaloalkanols such as 1,3-dichloroisopropanol; 1,3-dibromoisopropanol; sulfonium switterions such as the tetrahydrothiophene adduct of novolac resins, haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Also useful as cross-linking agents are monomeric amine-epihalohydrin adducts prepared by reacting at least two moles of an epihalohydrin with one mole of various monoamines, diamines and triamines at a temperature in the range from 0° to 90° C. for a time period of 0.5 to 8 hours. The reaction is carried out in a reaction medium containing 20 to 90 percent water, lower alcohols such as methanol or ethanol, or in aqueous solutions of the lower alcohols. The amine-epihalohydrin adducts are used directly as made without separation of concentration. The preparation and use of amine-epihalohydrin adducts as cross-linking agents is further disclosed in the patent application by L. R. Gross, Ser. No. 796,627 filed May 14, 1977, which application was refiled Dec. 22, 1980 and subsequently issued as U.S. Pat. No. 4,310,593. That application is incorporated by reference herein.

Sulfonium zwitterions are known from U.S. Pat. Nos. 3,660,431; 3,749,737 and 3,749,738. The disclosures of these patents are incorporated herein by reference.

Polyvalent metal cations can also be employed as cross-linking agents.

These cross-linking agents are used in an amount from about 0.05 to about 5.0 percent based on the weight of the polyelectrolyte used. This is generally sufficient to cause the polyelectrolyte to become lightly cross-linked.

It is sometimes desirable to add a small amount of a surfactant to the polyelectrolyte composition to aid in flowing on and removing the continuous film from the water-impervious substrate. A secondary benefit of using a surfactant is to increase the wettability of the final dry absorbent film. Either anionic or nonionic surfactants may be used. Examples of the useful surfactants are the sodium alkyl sulfonates and the ethylene oxide derivatives of alkylated phenols and the like.

Other hydrophilic polymers may also be employed, such as acrylic copolymer and starch/graft copolymers. Composites containing such polymers with wicking substrates are available commercially as Permasorb Sheet Laminate and Sanwet 1M-300 ® (a trademark of Sanyo Chemical Company). Also useful are the water-insoluble alkali salts of saponified, gelatinized starch-/polyacrylonitrile graft polymers taught in U.S. Pat. No. 3,997,484. Other such polymers will be known.

For the purpose of this invention, a moisture absorbent or water-swellable polyelectrolyte or polymer is defined as one which absorbs greater than about 15 times its weight of synthetic or natural urine. Preferably, the absorbance should be in the range from about 30–60 grams of urine per gram of polyelectrolyte or in the range of 90–250 grams of deionized water per gram of polyelectrolyte. The level of cross-linking agent used is a variable factor which is dependent upon the particular polyelectrolyte used and the molecular weight of the polyelectrolyte. Peferably, the amount used varies from 0.25 to 3.0 percent based on the weight of the polyelectrolyte. However, this range is varied for each polyelectrolyte in order to adjust the absorbency of the final cross-linked material.

The water-swellable polymer films of this invention may be combined with wicking or nonwicking substrates to one or both surfaces. Examples of wicking substrates include woven fabrics, nonwoven fiber mats, cellulose fluff, polymeric foams, tissue paper, crepe paper, paper wadding and paper toweling. Typical nonwicking substrates include polymer films, such as polyethylene film, and hard surface papers, such as kraft or writing paper.

The laminates are useful to make absorbent articles such as baby diapers, adult diapers for incontinent patients, catamenial devices and the like since the laminates and/or articles readily absorb aqueous solutions such as blood, urine, and other body exudates. The absorbent articles contain one or more layers of wicking substrates such as nonwoven fiber mats, tissue wadding, or cellulose fluff together with a water-impermeable bottom sheet such as polyethylene and a water-permeable top sheet such as a nonwoven fiber mat.

The films and laminates are frequently less soft and pliable than desired for use in articles that will be in contact with skin. The laminates can be run through a crushing or creping zone to fracture the film into a plurality of pieces that adhere to the wicking or non-wicking substrate. Such procedures require expensive machinery which may not be readily available.

The undesirable stiffness in the films and laminates can be mitigated according to this invention by applying an aliphatic hydroxyl compound having a boiling point of at least 100° C. to the surface in an amount to achieve the desired softness and flexibility. The application can be made with the hydroxyl compound itself or a water mixture containing at least 10 percent of that compound.

The useful aliphatic hydroxyl compounds are those which are relatively nonvolatile in having boiling points of at least 100° C. Water compatibility is desirable. Glycerin is most preferred. Other preferred compounds are the aliphatic polyols or derivatives thereof, typical of which are the glycols, glycol ethers and glycol esters. Representative compounds falling within those classes include ethylene glycol, propylene glycol, the methyl, ethyl or aryl ether of ethylene glycol, ethylene glycol monoacetate and glyceryl diacetate.

The application should provide from 10 to 50 weight percent hydroxy compound based on the weight of the polymer in the film or the composite. Application can be by spraying, padding, roll coating, gravure application or other known technique.

As a result of the application of the hydroxy compound, the film or laminate becomes softer and retains its water absorbency.

The inventive concept is illustrated in the following examples showing the best mode for carrying out the invention.

In the examples, the following test procedures were run:

a. Surface Absorption Rate

A sample of film or laminate at least 7×7 inches (17.2×17.2 cm) is placed flat on a level glass plate having a polyethylene film on its surface. A dam is placed upon the film or laminate and sealed to provide an enclosed area 6×6 inches. About 35 grams of a 1 percent aqueous sodium chloride solution (equal to about 75–85 percent of the capacity of a 36 square inch (232 square cm) sample) is poured into the enclosed area. A stopwatch is started and is stopped when all surface liquid disappears as noted by a loss of reflected light at an appropriate angle. The absorption rate is the time in seconds to absorb the liquid.

b. Absorption Capacity

A minimum of three samples are cut from across the width of a laminate sheet to give a sample size of approximately one gram dry weight. The moisture content of a separate specimen adjacent to those three is determined. Each sample is placed into a 250-ml beaker and 150±0.1 grams of 1 percent aqueous NaCl solution is added. Each is allowed to stand for 20 minutes with occasional light stirring to insure a uniform free-swell absorption. Each is filtered through a 150-mesh nylon or polypropylene screen into a tare-weighed container. Each is allowed to drain for 20 minutes making sure all the liquid from the beaker is transferred to the funnel containing the screen and absorbed gel. About two minutes before the end of the drain period, the screen and gel are raised slightly from the funnel to allow trapped liquid to drain. The container and filtrate (unabsorbed liquid) are weighed. The "free-swell" absorption capacity of the laminate is calculated as:

Capacity (q/ft²)=capacity grams solution/grams laminate×laminate weight g/ft² .

c. Laminate Softeners

A sample of the laminate is exposed to 20 percent relative humidity at 72° F. for a minimum of three hours before testing.

Three 8×8 inch (20.3×20.3 cm) test samples are cut from the laminate giving a sample from the center and edges. Care is taken to avoid creases which give abnormal values.

The test apparatus is a Handle-O-Meter ® with a 100-gram load cell. That apparatus is sold by Thwing-Albert Instrument Co. as Model 211-5.

After calibration, the laminate sample is placed on the plate and over the center of the plate with the right edge against the right plate wall. The force required to push the sample into the ⅜ inch (0.95 cm) wide plate slot is determined and recorded to the nearest 0.5 gram.

The sample specimen is tested in both the machine and transverse direction.

EXAMPLE 1

A water absorbent laminate (not embossed or needlepunched) prepared according to U.S. Pat. No. 4,117,184 is sprayed with a 50/50, by weight, blend of glycerin/water. The result is dried in the oven to remove excess moisture then is exposed to ambient humidity for 10 minutes before test runs are conducted. It retains most of its original (before glycerin treated) capacity. The rate is high for both the control (not treated with glycerin) and the glycerin treated sample.

|  | Not Embossed or Needlepunched | | | | | |
|---|---|---|---|---|---|---|
|  | Control | | | Glycerin Treated | | |
|  | Left | Center | Right | Left | Center | Right |
| Rate (Sec) | 240+ | 240+ | 240+ | 240+ | 240+ | 240+ |
| Softness (MD) | 88.5 | 101.3 | 97.3 | 16.1 | 19.0 | 16.2 |
| Softness (TD) | 72.5 | 74.3 | 67.0 | 16.0 | 17.0 | 15.6 |
| Capacity |  |  |  |  |  |  |
| (g/ft²) | 192 | 206 | 199 | 174 | 199 | 185 |
| (g/m²) | 2066 | 2217 | 2142 | 1872 | 2142 | 1991 |

Each of an embossed laminate and a needlepunched laminate (¼ inch centers) is treated with glycerin (sprayed) to determine if the rate would stay low. The data are tabulated below:

|  | Embossed Laminate | | Needlepunched Laminate | |
|---|---|---|---|---|
|  | Standard | Glycerin | Standard | Glycerin |
| Rate (Sec) | 36 | 35 | 25.3 | 25.0 |

Both softness and a low rate are desirable in an absorbent laminate.

EXAMPLE 2

Specimen swatches of the laminate of Example 1 are needlepunched on about ¼ inch (0.64 cm) centers. Different amounts of a 1 to 1 glycerin/water solution are sprayed onto the laminate which are then dried for 16 hours at 125° F. then exposed to ambient humidity. The specimens are then tested for softness with the Handle-O-Meter with the following results:

| % Glycerin | Softness |
|---|---|
| 0 | 105 |
| 10 | 100 |
| 15 | 70 |
| 20 | 65 |
| 25 | 35 |
| 30 | 25 |
| 50 | 25 |

EXAMPLE 3

A laminate is prepared from the same polymer film as Example 1 with tissue laminated to one of the film surfaces. A 50 percent glycerin-in-water solution is sprayed onto the film surface. Tissue is then adhered to that surface. The laminate is soft.

In like manner, different laminate samples are prepared using various ratios of a glycerin/water solution containing from 10 to 90 percent glycerin and 90 to 10 percent water. In all instances, the laminates are noticeably softer than untreated samples.

EXAMPLE 4

Examples 2 and 3 are repeated applying the glycerin with a roll coater instead of by spraying. The laminate in each instance is soft.

EXAMPLE 5

A glycerin/water solution is applied to one surface of a swatch of the laminate of Example 1 and to both surfaces of a different swatch of the same laminate. The softness is about equal in both cases.

EXAMPLE 6

A 50/50 glycerin/water mix is applied to commercially available absorbent composites. One composite is Permasorb sold by National Starch Co.; one is Water-Loc ® sold by Grain Processing Co. and one is believed to be a water-insoluble alkali salt of a saponified, gelatinzed starch/polyacrylonitrile graft polymer sold by Henkel et Cie. A soft composite is obtained as illustrated by the following Handle-O-Meter data:

|  | Standard | | Glycerin Applied | |
|---|---|---|---|---|
|  | MD | TD | MD | TD |
| Permasorb ® (a trademark of National Starch Company) | 43 | 49 | 25 | 26 |

|  | Standard | | Glycerin Applied | |
| --- | --- | --- | --- | --- |
|  | MD | TD | MD | TD |
| Water-Lock ® (a trademark of Grain Processing Company | 57 | 69 | 28 | 30 |
| Graft polymer | 68 | 75 | 37 | 43 |

A Handle-O-Meter value below 40 is considered soft.

EXAMPLE 7

Swatches on the laminate of Example 1 were sprayed on one side with a combination of 75 percent of a softener and 25 percent of water. The amount of softener applied was 27 percent by weight of the polymer. The treated samples were exposed to 40 percent relative humidity overnight and tested in a 40 percent relative humidity room. The results are noted in the following Handle-O-Meter data:

| Softener | TD | MD |
| --- | --- | --- |
| None | 60 | 57 |
| Glycerin | 23 | 22 |
| Ethylene Glycol | 23 | 23 |
| Propylene Glycol | 26 | 30 |
| Pycal 94* ® | 34 | 35 |
| Diacetin** | 32 | 35 |

*Pycal 94 ® (a trademark of ICI) is believed to be a polyoxyethylene aryl ether sold by ICI.
**Diacetin is glyceryl diacetate sold by Eastman Kodak Co.

What is claimed is:

1. A process for softening a dry film of a swellable hydrophilic polymer by applying a liquid aliphatic hydroxyl compound having a boiling point of at least 100° C. to the surface of said film in an amount of 10 to 50 percent based on the weight of said film.

2. The process of claim 1 wherein said hydroxy compound is applied from a blend of 10 to 100 percent compound and 90 to 0 percent water.

3. The process of claim 1 wherein said hydrophilic polymer is a carboxylic polyelectrolyte cross-linked with a water-soluble polyamido-polyamine/epichlorohydrin adduct.

4. The process of claim 3 wherein said carboxylic polyelectrolyte is an ammonium alkali metal salt of the homopolymers of acrylic acid or methacrylic acid.

5. The process of claim 3 wherein said carboxylic polyelectrolyte is an ammonium alkali metal of the interpolymers of acrylic or methacrylic acid with at least one monoethylenically unsaturated comonomer.

6. The process of claim 5 wherein said carboxylic polyelectrolyte is a terpolymer of ethyl acrylate, sodium acrylate and sodium methacrylate with 50 mole percent being ethyl acrylate.

7. The process of claim 1 wherein said hydrophilic film is a water-swellable aerated film comprising a lightly cross-linked alkali metal carboxylate having a density ranging from 1.1 to 0.3 grams per cubic centimeter.

8. The process of claim 1 wherein said film has a wicking substrate adhered to at least one surface thereof.

9. The process of claim 7 wherein said wicking substrate is a woven fabric, a nonwoven fiber mat or a polymeric foam.

10. The process of claim 8 wherein said wicking substrate is tissue paper.

11. The process of claim 8 wherein said hydrophilic film is substantially fractured with the film fragments adherent to said wicking substrate.

12. The process of claim 1 wherein said hydrophilic film is needlepunched on at least $\frac{1}{4}$ inch centers.

13. The process of claim 1 wherein said hydroxy compound is glycerin.

14. The process of claim 1 wherein said hydroxy compound is ethylene glycol.

15. The process of claim 1 wherein said hydroxy compound is propylene glycol.

16. The process of claim 1 wherein said hydroxy compound is polyoxyalkylene alkyl or aryl ether.

17. The process of claim 1 wherein said hydroxy compound is glyceryl diacetate.

* * * * *